United States Patent [19]

Tomiyama et al.

[11] Patent Number: 5,707,878
[45] Date of Patent: Jan. 13, 1998

[54] METHOD FOR DETECTING BLOOD COMPONENT USING CONIDIOBOLUS HEMAGGLUTININ

[75] Inventors: Tetsuo Tomiyama, Tokyo; Tadashi Narita, Shisui-machi; Takeshi Kotsugai, Sawara; Shigeo Narita, Hiratsuka, all of Japan

[73] Assignee: SS Pharmaceutical Co., Ltd., Tokyo, Japan

[21] Appl. No.: 464,625

[22] PCT Filed: Dec. 27, 1994

[86] PCT No.: PCT/JP94/02241

§ 371 Date: Jun. 26, 1995

§ 102(e) Date: Jun. 26, 1995

[87] PCT Pub. No.: WO95/18375

PCT Pub. Date: Jun. 7, 1995

[30] Foreign Application Priority Data

Dec. 28, 1993 [JP] Japan ................. 5-349054

[51] Int. Cl.⁶ .................. G01N 33/555; G01N 33/24
[52] U.S. Cl. .................. 436/520; 436/66; 435/14
[58] Field of Search ............. 436/520, 66; 435/14

[56] References Cited

U.S. PATENT DOCUMENTS

| | | | |
|---|---|---|---|
| 4,134,792 | 1/1979 | Boguslaski et al. | 195/99 |
| 4,857,457 | 8/1989 | Shamsuddin | 435/7 |
| 5,162,202 | 11/1992 | Shamsuddin | 435/25 |
| 5,179,004 | 1/1993 | Haselbeck et al. | 435/7.92 |
| 5,198,365 | 3/1993 | Grow et al. | 436/66 |

FOREIGN PATENT DOCUMENTS 0237366 11/1985 Japan.

OTHER PUBLICATIONS

Kay, MMB et al, Proc. Natl. Acad. Sci, USA, vol. 80, Mar. 1983 pp. 1631–1635.

England, BJ et al, Biochem et Biophys. Acta, 623, 1980, pp. 171–182.

Ishikawa, F. et al, Agric. Bio. Chem., 45(3), 1981, pp. 557–564.

Ando, K et al, Biochem et Biophys. Acta, vol. 1178, pp. 127–134, 1993.

Kay, MMB et al, Biomed. Biochem. Acta, vol. 43 (6) 1984, pp. 841–846.

Primary Examiner—James C. Housel
Assistant Examiner—Ginny Allen Portner
Attorney, Agent, or Firm—Oblon, Spivak, McClelland, Maier & Neustadt, P.C.

[57] ABSTRACT

A method for detecting blood component in a sample comprising reacting a human erythrocyte membrane band 3 glycoprotein (band 3) in the sample and a hemagglutinin produced by a microorganism belonging to the genus Conidiobolus (CA) and measuring said band 3 glycoprotein contained in a complex produced by the reaction. Because band 3 can be detected specifically, at high sensitivity, and stably by the use of CA, the method ensures qualitative or quantitative, and accurate detection of human blood component in feces or contents of digestive organs, of which the determination of the presence or quantity of human blood component by hemoglobin is difficult.

9 Claims, No Drawings

METHOD FOR DETECTING BLOOD COMPONENT USING CONIDIOBOLUS HEMAGGLUTININ

TECHNOLOGICAL FIELD

The present invention relates to a method for specifically detecting blood component derived from human and, more particularly, to a method for detecting a blood component capable of detecting minute bleeding in digestive tract for the purposes of screening, for example, the screening of colorectal cancer and the like, and a kit using this detection method.

BACKGROUND ART

Detection of blood component of human is required in a variety of fields. The necessity is especially important in the clinical field. Bleeding, for example bleeding in digestive tract, occurs in a variety of diseases. Particularly, it is well known that bleeding from digestive tracts is an important early stage symptom in malignant tumors of digestive tracts.

Detection of blood components in feces, especially hemoglobin, is a major method currently applied to the detection of digestive tract bleeding for diagnosis of diseases such as malignant tumors of digestive tracts. Reversed passive hemagglutination, latex agglutination (fixation), gold colloid agglutination, enzyme immunoassay, radio immunoassay, and the like are included in the methods for detecting the hemoglobin in stools. Their principle is preparing an anti-human hemoglobin antibody, causing an antigen-antibody reaction with hemoglobin, and measuring or detecting the resultant by various methods.

In the conventional immunological method for detecting hemoglobin using the anti-human hemoglobin antibody, however, the hemoglobin to be detected is usually supplied to the test together with feces which act as an inactivating factor. The antigenic determinant of hemoglobin may be inactivated depending on the temperature over time, resulting in a drawback of conspicuous deterioration of the detection sensitivity.

Hemoglobin may be denatured or decomposed, particularly under high temperature conditions in summertime, therefore, hemoglobin positive feces are often reduced to negative in summer {Takefumi FUJIYOSHI and Mariko KOYAMA, Kiso-to-Rinsho [CLINICAL REPORT (Basic and Clinical Report)] 23(15), 6097–6101 (1989), "Basic studies on immune stool occult blood reagent"}. The inactivation of hemoglobin is significant particularly when its concentration is low. It is difficult to perform hemoglobin detection which is meaningful for diagnosis in such low concentration levels.

Development of a method for properly measuring blood component in samples of feces or the like without being affected by temperatures, storage time and the like has been required. The object of the present invention is to provide such a method.

DISCLOSURE OF THE INVENTION

The present inventors have conducted extensive studies in order to detect blood or blood component in fecal samples or the like using a blood component other than hemoglobin.

As a result, the inventors have found that human erythrocyte membrane band 3 glycoprotein (hereinafter referred to as band 3) can be properly detected, because it is much mores table than hemoglobin even in samples of feces or the like, and forms a complex by binding with a certain hemagglutinin specific for human erythrocytes. This finding has led to the completion of the present invention.

Accordingly, the present invention provides a method for detecting a blood component in a sample comprising reacting band 3 in the sample and a hemagglutinin produced by a microorganism belonging to the genus Conidiobolus and measuring the complex produced by the reaction, and a kit used for the detection.

BEST MODE FOR CARRYING OUT THE INVENTION

Band 3 which is detected as a blood component in the method of the present invention is a component which has already been reported as an erythrocyte marker (Beppu, M. et al., J. Biol. Chem., 256(6), 3226–3233 (1990), "Binding of anti-band 3 autoantibody to oxidatively damaged erythrocytes", etc.) and been studied as useful for monitoring erythrocytes.

The hemagglutinin produced by a microorganism belonging to the genus Conidiobolus (hereinafter abbreviated as CA) is a human erythrocyte-specific hemagglutinin produced by a microorganism belonging to the genus Conidiobolus such as *Conidiobolus lamprauges*, *Conidiobolus nanodes*, or the like. This hemagglutinin has been reported to exhibit interactions with band 3 (Ishikawa, F. et al., Agric. Biol. Chem., 45(9), 2105–2110 (1981), "Action of proteases on human erythrocyte glycoproteins in relation to hemagglutination by Conidiobolus chitin-binding agglution"), but no blood detection method utilizing it has been known heretofore.

The method of the present invention comprises detecting human blood component in samples by detecting band 3 contained in a complex of band 3, which is a blood component in that sample, and CA. Any detection methods can be applicable inasmuch as the band 3 can be detected in that manner.

One of the embodiments for carrying out the present invention is a so-called sandwich method which comprises insolubilizing CA on the surface of a solid phase, adding the sample and a labeled anti-band 3 antibody which specifically binds with the same band 3 to sandwich the band 3 in the sample between the immobilized CA and the labeled anti-band 3 antibody, and identifying or measuring human blood via band 3 which has been present in the sample.

In this embodiment, it is possible to add the labeled anti-band 3 antibodies to the sample in advance as mentioned below.

In the above system, a certain peptide portion of the band 3 in the sample is recognized by an added anti-band 3 antibody, and sugar chain portion of the band 3 is separately recognized and captured by the immobilized CA. Further, another peptide portion of the band 3, which portion is different from the peptide portion initially recognized by the added anti-band 3 antibody, is recognized by a labeled anti-band 3 antibody. In this manner, the band 3 in the sample is determined by the anti-band 3 antibody, the immobilized CA, and the labeled anti-band 3 antibody, so that the band 3 can be highly restricted. This prevents cross-reaction with a variety of contaminating glycoproteins in samples resulting in an increase of sensitivity and the specificity.

The specific detection system in the present invention is not limited to the above embodiments. The immobilized component and the labeled component in the above embodiments may be replaced by using a combination of an immobilized anti-band 3 antibody and a labeled CA, or CA may be the immobilized component and the labeled component as well if a combination of an immobilized CA and a labeled CA is used. The methods similar to the above described embodiment can be applied to these cases for improving the sensitivity and the specificity.

Another embodiment of the method of the present invention is a detection method using a so-called competitive reaction. The method comprises capture of a labeled band 3 prepared in advance by the immobilized phase competitively along with capture of the band 3 in the sample by the immobilized phase, whereby the presence or absence or the quantity of blood in the sample can be detected by the label in the former band 3.

Any labeling method, Such as radioisotope labeling, enzyme labeling, fluorescence labeling, or light emitting chemical labeling, can be used for labeling the CA or anti-band 3 antibody. Specific methods include a method of labeling with biotin and detect it by a labeled avidin, a method of using a labeled second (other) antibody to CA or anti-band 3 antibody instead of labeling the CA or anti-band 3 antibody. There are no limitations to the specific detection system inasmuch as the labeling which enables the detection is given.

In the method of the present invention, it is possible to have the anti-band 3 antibody or CA present in the sample in advance, for example, by coating the surface of stool collecting sticks beforehand with a required quantity of anti-band 3 antibody or CA in a manner where they are capable of dissolving out.

Various buffer solutions, such as acetate buffer, phosphate buffer, Tris-HCl buffer, glycine buffer, ammonium buffer, borate buffer, and carbonate buffer, are given as examples of the base solution which solubilizes and dissolves band 3 from samples of feces or the like containing the same. The pH of these base Solution is in the range of 4–11.5, and preferably 4.5–8.5.

It is desirable to add sodium chloride to the base solution to make the content of it approximately the same as that of physiological saline. Further, it is desirable to add sodium azide or the like in an amount of 0.05–0.5% by weight as antibacterial agent. It is also desirable to add 0.05–2.0% by weight of bovine serum albumin or the like as a stabilizer for proteins such as antibodies.

Because the present invention is a method for detecting band 3 contained in human erythrocyte membrane, it is possible to use a surfactant as a solubilizer for solubilizing the erythrocyte membrane for detecting the band 3 more efficiently.

Examples of the surfactant which can be preferably used as the solubilizer in the present invention include, but not limited to, the following surfactants.

Sodium dodecylbenzene sulfonate
Polyoxyethylene-iso-octylphenyl ether (Triton X-100 etc.)
Polyoxyethylenenonylphenyl ether (Noident P-40 etc.)
Polyoxyethylenesorbitol ether (Tween 20 etc.)
3-[(3-Cholamidepropyl)dimethylammonio]-1-propane sulfonate
3-[(3-Cholamidepropyl)dimethylammonio]-2-hydroxy-1-propane sulfonate
n-Octyl-$\beta$-D-glucopyranoside
Octanoyl-N-methylglucamide
Nonanoyl-N-methylglucamide
Decanoyl-N-methylglucamide
n-Heptyl-$\beta$-D-thioglucoside
n-Octyl-$\beta$-D-thioglucoside
N,N-bis(3-D-gluconamidepropyl)deoxycholamide There are no specific limitations to the method for adding these surfactants. In the case where the above-mentioned buffers are used as the base solution, it is preferable to add a surfactant which can exhibit the effect at a concentration of less than 1% by weight.

The present invention is a method discovered for the first time for detecting human blood component in samples such as feces or the like via band 3 using CA and an anti-band 3 antibody, and particularly advantageous as a method for detecting fecal occult blood. As can be seen in the examples hereinafter, the fecal occult blood can be detected using this method at a higher sensitivity and more stably than the conventional stool occult blood detection method or the like using anti-hemoglobin antibodies.

The present invention will be illustrated more specifically referring to examples, which are not intended to be limiting of the present invention.

EXAMPLE 1

<Method for detecting band 3 in feces Using an enzyme labeled anti-band 3 antibody and CA>

(1) Purification and isolation of band 3

200 ml of O-type human blood to which an anticoagulant was added was centrifuged at 320×g for 10 minutes to separate plasma. The precipitate was suspended in 200 ml of a 0.05M phosphate buffer (pH 7.3) containing 1 mM EDTA, 5 mM 2-mercaptoethanol, and 0.03 mM phenylmethylsulfonyl fluoride, adjusted to pH 7.5 with 1M NaOH, stirred gently for 18 hours at 4° C., and centrifuged at 10,000×g for 1 hour. The precipitate was suspended in ice cooled water which had been adjusted to pH 12 with 1M NaOH. The suspension was stirred gently for 30 minutes at 4° C., and again centrifuged at 10,000×g for 30 minutes. The precipitate thus obtained was suspended in a 40 mM Tris-HCl buffer (pH 7.4) containing 1% sodium dodecyl sulfate, 2 mM EDTA and 0.04 mM 2-mercaptoethanol and allowed to stand at 4° C. for one hour, following which the temperature was allowed to raise to room temperature.

This suspension was passed through a Sepharose 6B column (made by Pharmacia, 2 cm$\phi$×98 cm) equilibrated with the above buffer, and fractions having absorbance at 280 nm were collected. The band 3 was eluted just before the elution of glycofolin A.

(2) Preparation of polyclonal antibody for band 3

Band 3 was dissolved in physiological saline to prepare a solution with a concentration of 4 mg/ml. The solution was subcutaneously injected into back of rabbits 8 times at an interval of 2 weeks, each time at a dose of 1 ml. Blood was collected 3 weeks after the final subcutaneous injection to obtain anti-band 3 antibody serum.

This anti-band 3 antibody serum was added to a Protein A Sepharose CL-4B column (made by Pharmacia, 1 cm$\phi$×14 cm) equilibrated with a 20 mM Tris-HCl buffer (pH 8.3.) containing 0.2M NaCl and the column was eluted with the same buffer solution to collect fractions. The elution was continued until the absorbance at 280 nm returned to the initial standard level.

Next, this column was eluted with a 0.1M glycine-HCl buffer (pH 3.0) to collect fractions until the absorbance at 280 nm returned to the initial standard level. Fractions which was determined to contain the protein based on the absorbance was pooled and dialyzed against a 10 mM phosphate buffer (pH 7.5).

The antibody thus obtained was confirmed by the Ouchterlony method to possess specificity to band 3 derived from human erythrocyte (this antibody is hereinafter referred to as "anti-band 3 antibody").

(3) Labeling the anti-band 3 antibody with an enzyme

Horse radish peroxidase (a product of Sigma Co., hereinafter abbreviated to HRPO) was bonded to the anti-band 3 antibody according to the following method.

The HRPO was dissolved into a 10 mM acetate buffer (pH 4.5) to a concentration of 15 mg/ml, and sodium metaperiodate was added to this solution to a final concentration of 33 mM. The mixture was incubated at 25° C. for 15 minutes and passed through a Sephadex G-25 column (made by Pharmacia, 1 cm$\phi$×14 cm) equilibrated with the same acetate buffer as above to collect eluted fractions with a brown color. The fraction was confirmed to be the activated HRPO.

The activated HRPO fractions were adjusted with said acetate buffer as above to obtain a final concentration of 1 mg/ml. This was added to an equivalent amount of a solution of the anti-band 3 antibody which had been adjusted to a concentration of 4 mg/ml with a 50 mM carbonate buffer (pH 9.5), and the mixture was incubated at room temperature for 4 hours.

The reaction was retarded by the addition of sodium borohydride to a final concentration of 2.6 mM and the reaction was continued for 30 minutes at 4° C. under the retarded conditions. The reaction of sodium borohydride was terminated by the addition of acetone to a final concentration of 0.2% (v/v) thus obtaining a HRPO labeled anti-band 3 antibody.

(4) Preparation of CA

*Conidiobolus lamprauges* CBS 153,56 stocks were inoculated into test tubes with an internal diameter of 16 mm, each containing 5 ml of 0.05M phosphate buffer (pH 7.0) containing 1% lactose, 0.5% peptone, 0.3% yeast extract, and 0.3% malt extract, and cultured for 3 days at 27° C. on a reciprocal shaker at 120 rpm. 5 ml of the culture broth was inoculated into each of 500 ml Sakaguchi shaker flasks to which 100 ml of the same phosphate buffer as above was added, and further cultured for 5 days at 27° C. on a rotating shaker at 120 rpm.

The culture broth was filtered through a filter paper to separate cells. Solid ammonium sulfate was added to 3000 ml of the filtrate at 0.75 saturation with ice cooling and the mixture was allowed to stand overnight at a low temperature. The precipitate produced was collected by centrifuge for 20 minutes at 10,000×g, dissolved in a 0.05M phosphate buffer (pH 6.0), and dialyzed against the same buffer overnight. Insoluble matters produced were removed by centrifuge for 20 minutes at 10,000×g, thus obtaining 142 ml of supernatant.

This solution was passed through CM-Sephadex C-50 column (made by Sigma Co., 2 cm$\phi$×98 cm) equilibrated with the same buffer as above to collect a fraction eluted gradiently with 0.05–0.5M of the above buffer solution. Hemagglutination activity of CA of the fraction was determined. 67 ml of this fraction was applied to a Sepharose 4B column (made by Pharmacia., 1 cm$\phi$×14 cm) with $\beta$-N-acetyl-D-glucosamine bonded and equilibrated with a 1M NaCl –0.05M phosphate buffer (pH 6.0). After washing the column with the same buffer, the column was eluted gradiently with 0–0.36M N-acetylglucosamine solution. Among the fractions eluted, a portion obtained initially in the gradient elution was used as a purified CA sample.

(5) Immobilization of CA

A 2 µg/ml CA solution (.0.1 mol Tris-HCl buffer, pH 8.4) was charged into a microplate in an amount of 150 µl per well and allowed to stand overnight at 4° C. to adsorb and immobilize (insolubilize) CA on the microplate surface.

(6) Preparation of fecal samples

Sample 1 was prepared by mixing 2 g of feces of a healthy adult and 8 µl of human blood. Sample 2 was prepared by diluting Sample 1 to a ¼ concentration, i.e., by mixing about 0.5 g (¼) of the sample with 1.5 g of the feces of the healthy adult. Sample 2 was diluted in the same manner to a concentration of ¼ to prepare Sample 3 (¹⁄₁₆ dilution of Sample 1). Feces containing no blood was used as a sample blank (Sample 4).

Accordingly, the amounts of blood added were 4 µl 1 µl, 0.25 µl, and 0 µl per 1 g of feces.

(7) Preparation of sampling solution

A 0.1 mol/1 Tris-HCl buffer solution (pH 8.0) containing 1% Triton X-100 (made by Sigma Chemical), 0.1% sodium azide, 0.1% bovine serum albumin, and 0.9% sodium chloride was prepared and charged to test tubes to be used as the solution for the samples, in an amount of 2 ml per tube.

(8) Collection of samples and preparation of sample solutions

Feces sampling sticks were inserted into sample feces to collect samples, each about 10 mg. Each sample was then suspended in 2 ml of the sampling solution and incubated at 37° C. for 5 minutes to prepare sample solutions.

(9) Measurement

The immobilized CA plate obtained in (5) mentioned above was washed with 0.1 mol Tris-HCl buffer (pH 8.4). The sample solutions prepared in (8) were added to the plate in an amount of 100 µl/well, followed by the addition of 50 µl/well of 0.5 mol acetate buffer (pH 4.5). The mixtures were incubated at 37° C. for one hour to capture band 3 in the sample solutions.

After thoroughly washing each well with a 0.1 mol phosphate buffer (pH 6.8), a HRPO labeled anti-band 3 antibody solution (a solution of 1 µg/ml HRPO labeled anti-band 3 antibody in 0.1 mol phosphate buffer (PH 6.1) containing 2% bovine serum albumin) was added in an amount of 150 µl per well, and the mixture was incubated at 37° C. for one hour.

Next, after again thoroughly washing with a 0.1 mol phosphate buffer (pH 6.8), a substrate solution (0.05M acetate buffer (pH 4.5) containing 0.03% o-phenylenediamine and 0.01% hydrogen peroxide) was added in an amount of 150 µl per well, followed by incubation at 37° C. for 30 minutes. The reaction was terminated by the addition of 50 µl/well of 4N hydrochloric acid. Absorbances were measured at two wavelengths, 492 nm and 630 nm, using a spectrophotometer (a microplate reader manufactured by Corona Co.). Band 3 in Samples 1–3 showed absorbance of 0.5 or larger against the sample blank, so that these were apparently positive.

COMPARATIVE EXAMPLE 1

<Detection of fecal occult blood using anti-hemoglobin antibody (conventional method)>

(1) Preparation of a latex reagent sensitized with anti-human hemoglobin antibody 10 ml of 1 mg/ml 1-ethyl-3-(3-dimethylaminopropyl)-carbodiimide was added to 10 ml of 5% carboxylated polystyrene latex and the mixture was reacted for 20 minutes while stirring. After separating out supernatant by centrifuge, an equivalent amount (10 ml) of 0.01 mol/l borate buffer was added to the precipitate latex. The mixture was stirred to homogenize, centrifuged to remove the supernatant. This procedure was repeated again, and finally the latex was dispersed in 10 ml of said buffer solution.

To 10 ml of the latex suspension (concentration: 5%) was added 7 ml of anti-human hemoglobin antibody (Rabbit IgG, concentration: 5 mg/ml), prepared by immunizing rabbit with purified human hemoglobin $A_o$, and the mixture was reacted for 5 hours while slowly stirring. The supernatant was removed by centrifuge. 10 ml of a 0.01 l borate buffer (pH 8.0) containing 0.1% bovine serum albumin was added to the precipitate latex. The mixture was stirred and then centrifuged to remove the supernatant. This procedure of removing supernatant by centrifuge was repeated again. Then, after adding 10 ml of said buffer, the mixture was stirred to obtain a latex reagent sensitized with anti-human hemoglobin antibody (latex concentration: 1%).

(2) Immunological latex agglutination reaction

Fecal sample solutions prepared in Example 1(8) were placed on each serological reaction slide glass plate in an amount of 100 μl each. 25 μl of the latex reagent as above was added to each, and, after 5 minutes mixing with rotation, the agglutination images were observed by naked eyes (macroscopically). As a result, the agglutination images were seen in Samples 1 and 2, but not in Samples 3 and 4, indicating that the sensitivity is inferior to the method of the present invention.

The results of Example 1 and Comparative Example 1 are summarized in Table 1.

TABLE 1

| | Blood concentration (μl/g stool) | Conventional method (Comp. Ex. 1) | Method of this invention (Example 1) |
| --- | --- | --- | --- |
| Sample 1 | 4 | + | + |
| Sample 2 | 1 | + | + |
| Sample 3 | 0.25 | − | + |
| Sample 4 | 0 | − | − |

−: Fecal occult blood, negative (samples exhibiting negative agglutination reaction in the conventional method or samples exhibiting absorbance of 0.4 or less against the sample blank in the method of the present invention.
+: Fecal occult blood, positive (samples exhibiting positive agglutination reaction in the conventional method or samples exhibiting absorbance of 0.5 or more against the sample blank in the method of the present invention.

EXAMPLE 2

<Comparison of the present invention and conventional method>

Sample 1, Sample 2, Sample 3, and Sample 4 (sample blank) prepared in Example 1(7) were incubated at 37° C. for 6 days, while measuring and comparing the presence of blood by the method of the present invention in Example 1 and the conventional method of Comparative Example 1 every day. The results are shown in Table 2.

TABLE 2

| | Incubation at 37° C. (days) | | | | | | |
| --- | --- | --- | --- | --- | --- | --- | --- |
| Measurement method | 0 | 1 | 2 | 3 | 4 | 5 | 6 |
| Sample 1 | | | | | | | |
| Invention method | + | + | + | + | + | + | − |
| Conventional method | + | + | − | − | − | − | − |
| Sample 2 | | | | | | | |
| Invention method | + | + | + | + | + | − | − |
| Conventional method | + | − | − | − | − | − | − |
| Sample 3 | | | | | | | |
| Invention method | + | + | + | + | − | − | − |
| Conventional method | − | − | − | − | − | − | − |
| Sample 4 | | | | | | | |
| Invention method | − | − | − | − | − | − | − |
| Conventional method | − | − | − | − | − | − | − |

−: Fecal occult blood, negative (samples exhibiting negative agglutination reaction in the conventional method or samples exhibiting absorbance of 0.4 or less against the sample blank in the method of the present invention.
+: Fecal occult blood, positive (samples exhibiting positive agglutination reaction in the conventional method or samples exhibiting absorbance of 0.5 or more against the sample blank in the method of the present invention.

The above results shows that, when incubated at 37° C., according to the method of the present invention the period of time for which a blood component can be detected at higher sensitivity was extended by utilization of band 3 while according to the conventional method hemoglobin was detected for only one day or so. It was confirmed that stable detection was possible according to the method of the present invention over a long period of time even in the case where the sample was continuously held at 37° C.

Industrial Applicability

As illustrated above, according to the detecting method of the present invention band 3 can be detected specifically, at high sensitivity, and stably by the use of CA. It is thus possible to qualitatively or quantitatively detect human blood component in feces, contents of digestive organs, and other materials in which the presence of human blood is questioned, or, so detect digestive tract bleeding, occult blood in feces, and the like, at high accuracy.

We claim:

1. A method for detecting a blood compound in a sample, comprising the steps of:
   1) reacting a) a sample suspected of containing human erythrocyte membrane band 3 glycoprotein,
      b) hemagglutinin produced by a microorganism belonging to the genus Conidiobolus, and
      c) an antibody specific for the human erythrocyte membrane band 3 glycoprotein, and
   2) measuring the presence of band 3 glycoprotein contained in the sample,
   wherein the presence of band 3 glycoprotein is indicative of the presence of a blood component in said sample.

2. The method for detecting blood component according to claim 1, wherein said hemagglutinin produced by said microorganism belonging to the genus Conidiobolus is immobilized.

3. The method for detecting blood component according to claim 1, wherein said antibody which can specifically combine with human erythrocyte membrane band 3 glycoprotein is a labeled antibody to the human erythrocyte membrane band 3 glycoprotein.

4. The method for detecting blood component according to claim 1, wherein said hemagglutinin is detectably labeled.

5. The method for detecting blood components according to claim 1, wherein measuring is carried out by a competitive reaction with a labeled human erythrocyte membrane band 3 glycoprotein.

6. A kit for detecting blood components in a sample comprising,
   (a) an immobilized hemagglutinin produced by a microorganism belonging to the genus Conidiobolus, and
   (b) a labeled antibody to human erythrocyte membrane band 3 glycoprotein.

7. A kit for detecting blood component in a sample comprising,
   (a) a hemagglutinin produced by a microorganism belonging to the genus Conidiobolus and labeled, and
   (b) an immobilized antibody to human erythrocyte membrane band 3 glycoprotein.

8. The method according to claim 1, wherein said sample comprises feces.

9. The method according to claim 1, wherein said antibody is immobilized.

* * * * *